(12) United States Patent
Rosero

(10) Patent No.: US 7,927,869 B2
(45) Date of Patent: Apr. 19, 2011

(54) SYSTEM AND METHOD FOR SUPPORTING A BIOLOGICAL CHIP DEVICE

(76) Inventor: Spencer Z Rosero, Pittsford, NY (US)

( * ) Notice: Subject to any disclaimer, the term of this patent is extended or adjusted under 35 U.S.C. 154(b) by 796 days.

(21) Appl. No.: 11/564,513

(22) Filed: Nov. 29, 2006

(65) Prior Publication Data

US 2007/0254004 A1 Nov. 1, 2007

Related U.S. Application Data

(60) Provisional application No. 60/794,217, filed on Apr. 20, 2006.

(51) Int. Cl.
*C12M 1/00* (2006.01)
*C12M 3/00* (2006.01)

(52) U.S. Cl. ............... 435/303.1; 435/286.4; 435/286.7

(58) Field of Classification Search ........... 435/3, 286.4, 435/286.5, 286.7, 303.1, 423; 165/159, 160
See application file for complete search history.

(56) References Cited

U.S. PATENT DOCUMENTS

| | | | |
|---|---|---|---|
| 5,474,552 A | | 12/1995 | Palti |
| 5,711,861 A | | 1/1998 | Ward et al. |
| 5,874,219 A | | 2/1999 | Rava et al. |
| 5,989,913 A | * | 11/1999 | Anderson et al. ............. 435/394 |
| 6,605,039 B2 | | 8/2003 | Houben et al. |
| 6,642,019 B1 | * | 11/2003 | Anderson et al. ............... 435/41 |
| 6,650,919 B2 | | 11/2003 | Edelberg et al. |
| 6,673,596 B1 | | 1/2004 | Sayler et al. |
| 6,884,215 B1 | | 4/2005 | Carash |
| 6,958,809 B2 | | 10/2005 | Sterling et al. |
| 2002/0055166 A1 | * | 5/2002 | Cannon et al. ............. 435/286.5 |
| 2004/0186359 A1 | | 9/2004 | Beaudoin et al. |
| 2004/0226881 A1 | * | 11/2004 | Miyazaki et al. ............. 210/615 |
| 2005/0026134 A1 | * | 2/2005 | Miller et al. ...................... 435/3 |
| 2005/0033126 A1 | | 2/2005 | Carash |
| 2005/0153273 A1 | | 7/2005 | Wiskwo et al. |
| 2005/0197554 A1 | | 9/2005 | Polcha |

* cited by examiner

*Primary Examiner* — William H Beisner
*Assistant Examiner* — Michael Hobbs
(74) *Attorney, Agent, or Firm* — Hodgson Russ LLP

(57) ABSTRACT

A support apparatus for maintaining, storing, and transporting biological materials, such as cells. In accordance with certain embodiments of the invention, the biologic materials may be integrated to an electronic component to form a biological chip device, which may be supported, transported, and adapted for interconnection with other such devices through the use of a support apparatus in accordance with embodiments of the invention. In certain embodiments, the support apparatus can generate signals and/or translate signals received for processing and/or relaying to another device or module (e.g., another support apparatus). A plurality of biological chip devices and associated support apparatuses can be supported and linked in a network to perform various desired functions.

45 Claims, 7 Drawing Sheets

US 7,927,869 B2

SYSTEM AND METHOD FOR SUPPORTING A BIOLOGICAL CHIP DEVICE

CROSS REFERENCE TO RELATED APPLICATIONS

This application claims priority to U.S. Provisional Application Ser. No. 60/740,564, filed Nov. 29, 2005, and to U.S. Provisional Application Ser. No. 60/794,217, filed Apr. 20, 2006, the contents of which are incorporated by reference in their respective entireties.

FIELD OF THE INVENTION

Certain embodiments of the invention relate generally to an apparatus, system, and method for supporting and transporting biological materials associated with biological chip devices, and for forming a network of interconnections between such materials and/or devices.

BACKGROUND SECTION

Recent advances in molecular biology, power supplies, and miniaturization of electronics have allowed the integration of biologic materials with electronics on a common platform. The integration of biological materials, such as living tissue and cells, with electronics may find applicability in a number of medical device technologies, for example.

A biological chip device or module is comprised of an electronic component (e.g., microprocessing devices, integrated circuits, logic devices and the like) and a biologic materials component (e.g., living tissue, cells and the like). The biological chip device or module may form a portion of an implantable device. The electronic component provides the device with the ability to communicate (e.g., to provide sensing and stimulation capability) with the biologic materials component and/or with other devices. The biologic materials component may consist of cells of interest (e.g., cardiac and vascular cells), which are obtained (e.g., biopsied) from a donor and/or a patient.

Biological chip devices are described in international patent application PCT/US2005/015380 and in U.S. patent application Ser. No. 11/397,627, relevant portions of which are hereby incorporated by reference in their respective entireties.

SUMMARY OF INVENTION

The specificity and sensitivity of implanted and external medical devices may be improved by using biologic tissue (e.g., living cells) as a sensor integrated into the device. The biologic tissue or cells may have characteristics that enable them to process multiple inputs and/or generate multiple outputs. In addition, the use of living cells may allow for the miniaturization of such devices when integrated with an electronic component or circuit, which may then translate the cell responses to electronic signals, for example. The use of a biologic component as part of a sensing device may improve sensitivity and/or specificity by producing responses to stimuli that are physiologic in nature.

Biologic materials may be supported, stored, and transported through the use of a support apparatus in accordance with certain embodiments of the invention. The biologic materials may additionally be integrated to an electronic component or circuit (e.g., a printed circuit board) to form a biological chip device, which may be supported, transported, and adapted for interconnection with other such devices through the use of a support apparatus in accordance with embodiments of the invention. The support apparatus may be formed of various shapes and sizes for particular applications. In some embodiments, the support apparatus may test the health of biological materials being supported therein, and may be able to alter the environment in response to such tests to maintain or sustain the biological materials. The support apparatus and biological chip device may be adapted to generate signals and/or translate signals received to a predetermined format for processing and/or relaying to another device or module (e.g., another support apparatus). A plurality of biological chip devices and associated support apparatuses can be supported and linked in a network, for example, to perform desired functions. Communication between devices can be accomplished via fluid flow between support apparatuses, by radio frequency, fiberoptic, and/or electrical signals, and possibly using blood as a communication medium, or by direct metallic conducting media (e.g., wires), or a combination of the above. A support apparatus according to some embodiments of the invention may be adapted to be implanted in a patient to function as an implantable medical device (IMD), or as a component in an IMD system. Certain embodiments of the invention include a biological chip device adapted to be supported, stored, and transported in a support apparatus.

Biologic materials associated with a biological chip device may be grown in a complex collagen or other biocompatible support matrix. Thus, a support apparatus according to certain embodiments of the invention may include a support matrix lined with sensing electrodes able to sense/measure various parameters such as acceleration, pressure, flow, temperature, strain/shear stress, and electrical signals, for example without limitation. The support matrix may be adapted to suspend biologic materials (e.g., cells) in three dimensions, for example, allowing biologic materials to respond in a natural or physiological manner.

DETAILED DESCRIPTION SECTION

Figure 1:
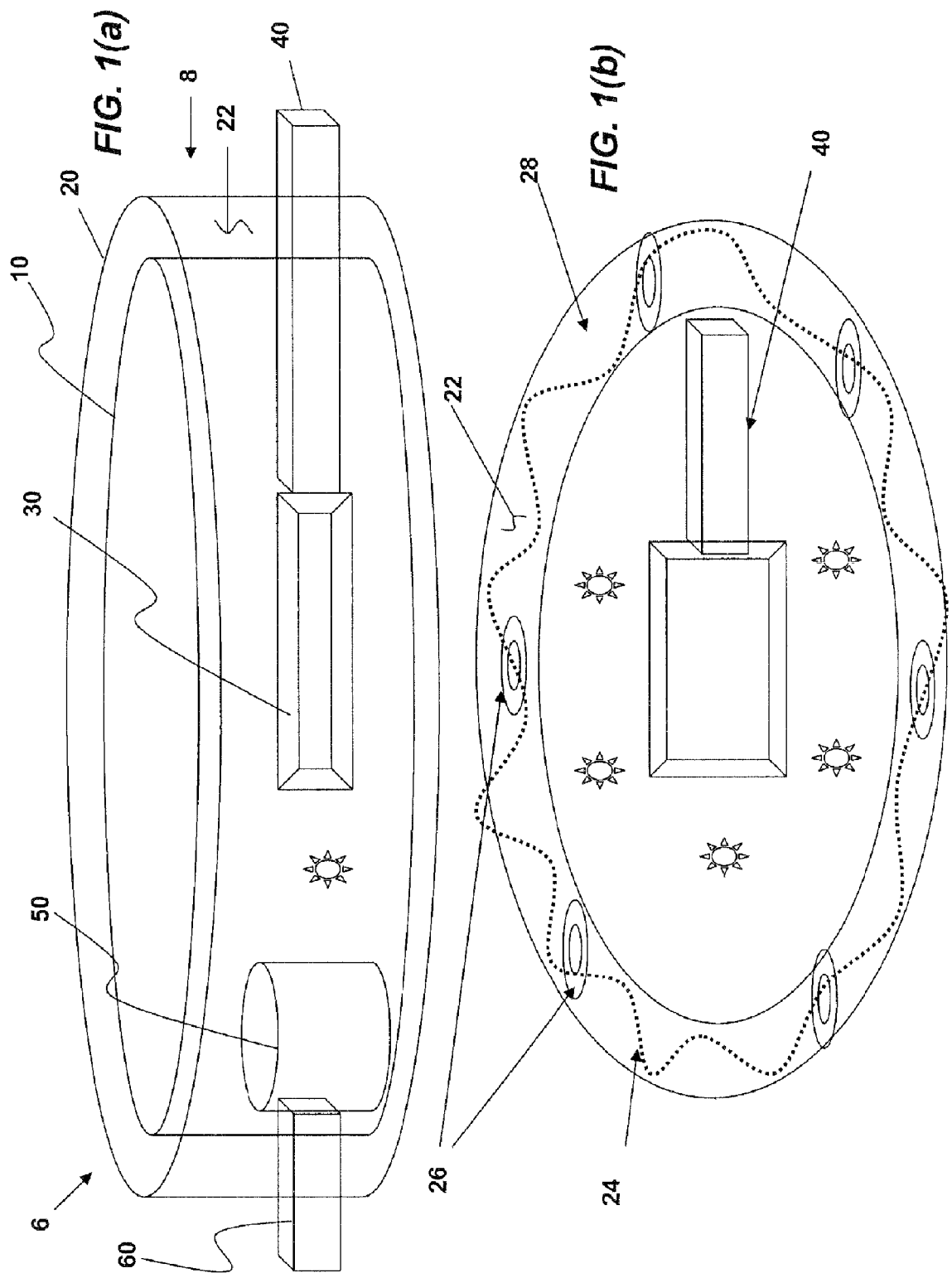
FIGS. 1(a) and 1(b) are schematic views of a support apparatus for supporting, storing, and transporting biologic materials in accordance with embodiments of the invention.

The following detailed description should be read with reference to the drawings, in which like elements in different drawings are numbered identically. The drawings depict selected embodiments and are not intended to limit the scope of the invention. It will be understood that embodiments shown in the drawings and described below are merely for illustrative purposes, and are not intended to limit the scope of the invention as defined in the claims.

Embodiments of the invention may include a device for supporting a biological chip device comprising a biologic materials component, and optionally, an electronic component. The device may, for example, be adapted for use as an implantable medical device (IMD), and may form at least a portion of an IMD system. The electronic component may be adapted to communicate with the biologic materials component. For example, the electronic component may be able to "sense" signals produced by the biologic materials component, and/or may be able to "send" signals (e.g., via electrical stimulation) to the biologic materials component. The biologic materials component comprises living cells of interest (e.g., cardiac, vascular, etc.) which are obtained from a patient (or donor) and sustained in a biocompatible support matrix, which may include a complex collagen. The support matrix may have sensing electrodes (which may be micron-sized) that sense various parameters such as acceleration, pressure, flow, temperature, strain/shear stress and electrical discharge/signals.

The support matrix may be of various shapes and/or sizes, and may be otherwise individualized for particular applications. The support matrix may, for example, provide for a three-dimensional arrangement of cells (e.g., supported by a complex collagen), which may allow for cellular responses and/or interactions between cells that more closely resemble natural, physiological responses and interactions. The support matrix may be coupled to an electronic component or circuit, for example a printed circuit board, that can generate signals and/or translate signals received from the support matrix (e.g., communicated from the biologic materials component) to a predetermined format for processing and/or relaying to another module. A plurality of individual support matrix devices can be linked together in a network as needed to perform desired functions and/or process and/or communicate desired information. Communication between support matrix devices can be accomplished, for example without limitation, via radio frequency, fiberoptic, and electrical signals (e.g., analog electrical subcutaneous signaling), using an available fluid (e.g., blood) as a communication medium, either alone or in combination with direct metallic conducting media (e.g., wires).

The specificity and sensitivity of such devices may be improved by using biologic tissue itself as the signal specific sensor that is integrated into the device. The biologic cells that form the biological materials component of the device may have characteristics which can enable the device to manage multiple inputs and outputs, for example. In addition, the cells may allow for miniaturization of the device when coupled with an electronic circuit that then translates the individual cell responses into a digital signal.

Certain embodiments of the invention provide a device or system for the storage, support, and transportation of biological chip devices. A device or system in accordance with certain embodiments of the invention may provide the "life-support" (including, for example, the supply of nutrients by a nutrient source, removal of waste, and maintenance of environmental conditions) required for each device, and can maintain the environment to allow the biological material to survive in various conditions. Environmental parameters that may be controlled include, but are not limited to, temperature, viscosity, pH, light (e.g., stimulation and/or protection via wavelength-specific filters), fluid cycling, and various gas levels (e.g., oxygen, nitrogen, etc.). Environmental parameters may be further controlled by the inclusion of filters for removal of waste products, compartments that provide (e.g., by eluting) nutrients such as glucose, energy components, etc., and algorithms for circadian control of various environmental parameters, such as temperature.

Certain further embodiments of the invention provide for a method of interconnecting a plurality of such support devices to form networks that may be able to receive, store, process, and/or generate signals.

FIG. 1(a) shows a partial cut-away schematic view of a support apparatus 6 for supporting biological materials (e.g., biological materials associated with biological chip devices) according to an embodiment of the invention. In the embodiment shown in FIG. 1(a), support apparatus 6 includes a support container (housing) 8, which may have an inner portion 10 and an outer portion 20. Inner portion 10 is disposed substantially within a volume defined by outer portion 20 such that a space 22 is formed between the inner and outer portions 10, 20. Inner and outer portions 10, 20 may be formed in a variety of shapes, such as generally cylindrical, generally rectangular or cubical, generally spherical, or any other shape suitable for a particular application. Further, the shape of inner portion 10 may be different from that of outer portion 20, and need not be centered within outer portion 20.

A biological chip device 30 is shown in FIG. 1(a) disposed within the inner portion 10, the biological chip device 30 being coupled to a connection strut 40. The connection strut 40 provides connections for providing one or more "services" to the biological chip device 30, such as providing an electrical power source, or sending and/or receiving signals (i.e., electronic signals, electro-optical signals, signals in the form of electromagnetic energy, test signals, etc.) to and from the biological chip device 30. The connection strut 40 couples the biological chip device 30 disposed in the inner portion 10 to a space outside the outer portion 20 of the housing 8. This may be done, for example, by allowing the connection strut 40 to pass through the walls of the inner and outer portions 10, 20, as shown schematically in FIG. 1(a). Alternately, at least a portion of the services may be contained within the inner portion 10, or in the space 22 between the inner and outer portions 10, 20. For example, electromagnetic energy, such as radio frequency (RF) energy, may be communicated to a portion of the connection strut 40 situated within the inner portion 10.

FIG. 1(a) also illustrates a fluid exchange 50 which may be disposed in the inner portion 10, with a fluid transfer conduit 60 that allows for the exchange (i.e., the delivery and/or removal) of gases and other fluids (e.g., oxygen, carbon dioxide, plasma, blood, nutrients, etc.) from outside the outer portion 20 into the inner portion 10, and vice versa.

FIG. 1(b) is a schematic plan view of the support apparatus 6 of FIG. 1(a) according to an embodiment of the invention. In the embodiment shown in FIG. 1(b), space 22 between the inner portion 10 and the outer portion 20 is shown having at least one thermal control element 24 (e.g., a heating element and/or a cooling element) disposed therein. Thermal control element 24 may comprise a fluid flow path (e.g., a coolant path that allows for heat exchange within space 22), or may include electrically resistive elements adapted to provide heat to space 22 (e.g., when electrical current is caused to flow). In some embodiments, a fluid (e.g., a gel or similar substance) may be placed in the space 22 in order to provide desired thermal characteristics. For example, a particular gel may provide a good thermal insulation layer to protect biological materials disposed within inner portion 10 from extreme temperatures. Alternately, a gel may be chosen due to its ability to conduct thermal energy, thereby enhancing the ability to control the temperature of the biological materials using the thermal control elements 24, for example.

In certain embodiments, one or more environmental sensors 26 may also be disposed within space 22. In certain preferred embodiments of the invention, a plurality of environmental sensors 26 may be disposed within the space 22 to monitor such environmental parameters as temperature, pressure, radiation (e.g., ultraviolet radiation), fluid/gas flow, pH, salinity, oxygen level, carbon dioxide, glucose, etc.

Environmental sensors 26 located within space 22 may be adapted to monitor and control the environment within the inner portion 10, but may also be able to respond to instructions (e.g., software-based instructions) for carrying out certain tasks. For example, diagnostic checks of the biological chip device 30 may be performed as a series of software-based instructions that may, for example, transiently lower the ambient temperature of the biological chip device 30 in order to obtain response data at various temperatures to compare with control ("normal") values, or to run calibration tests. The support apparatus 6 may be similarly adapted to release a chemical substance to the biological chip device 30 in response to certain instructions, for example, to trigger a cell response to perform a calibration check or to check the viability of the living cells.

In certain embodiments of the invention, the thermal control element 24 may be adapted to automatically respond to signals from certain of the environmental sensors 26, for example, by providing heating or cooling to the support housing 8 when temperature in the space 22 reaches predefined setpoints. For example, thermal control element 24 may comprise heating elements and/or cooling elements that may control the temperature in the space 22 (and indirectly, the temperature within the inner portion 10) by alternately energizing and de-energizing the heating and/or cooling elements in response to signals from the environmental sensors.

In certain embodiments of the invention, the space 22 between the inner portion 10 and the outer portion 20 may contain a fluid 28, such as a gel, to provide thermal insulation (i.e., to protect the inner portion 10 from changing environmental conditions outside the outer portion 20, for example), and/or to facilitate heat transfer (i.e., to raise or lower the temperature of the inner portion 10 via the thermal elements 24, for example).

The support housing 8 of support apparatus 6 may include water-proof and/or air tight control, for example, on fluid transfer conduit 60, which may optionally include venting capabilities in certain preferred embodiments. In certain embodiments, inner portion 10 and/or outer portion 20 may be formed of, or may include, insulated walls to further facilitate temperature control. In certain preferred embodiments, the ability to lower temperatures sufficiently to enable cryogenic storage capabilities may be provided, and may further provide a gradual warming capability to prepare the biological materials component of a biological chip device for use (e.g., for implantation).

The support housing 8 may include any or all of the following, according to various embodiments of the invention:

A holding portion within inner portion 10 adapted to hold biological materials (e.g., the biological materials component of a biological chip device) in a location that facilitates fluid contact with the biological materials;

A connection to a biological chip device (preferably water-proof) that allows the biologic materials to be exposed to a sustaining environment, while protecting the electronic components;

The connection may further provide micro electromechanical systems (MEMS) power as well as feedback on conditions of the biologic component of the chip; this would allow for testing of both the circuit and biologic/cellular responses;

The connection to the biological chip device may further include a viral/bacterial filter, for example a high efficiency particulate air (HEPA) filter screen;

The support housing 8 may include excitation emitters (e.g., light emitters) that can be adapted to test cellular response and allow for calibration of the biological chip device;

The support housing 8 may be translucent in some embodiments (e.g., either the inner portion 10, the outer portion 20, or both portions); in certain preferred embodiments, it may incorporate appropriate light filtering to prevent damage to cells from ultra-violet (UV) radiation, for example; and The support housing 8 and/or certain associated components may be adapted to be reusable, for example, by use of selected materials and design of components to enable sterilization and re-use.

Each support apparatus 6 may have its own power supply, which may also be adapted to be plugged in to an external source of power. Batteries, such as those used in medical and/or military applications, may be employed as power supplies. Batteries may be rechargeable, according to certain embodiments of the invention. For example, an AC adapter may allow a rechargeable battery to be recharged from a standard AC outlet via a transformer. In certain embodiments of the invention, charging or re-charging of the power supply for the biological chip device 30 may occur while in storage to preserve the power supply until needed.

In certain preferred embodiments of the invention, the support containers 8 may be reusable. Alternately, other embodiments of the invention may include disposable support containers 8. Reusable support housings or containers may include the ability to be hermetically sealed, including where access is needed for connections to the biological chip device 30. For example, a spring-loaded contact on the support apparatus 6 may allow for a hermetically-sealed "header" similar to those found on cardiac pacemakers and implantable defibrillators. Such a configuration would provide isolation of the support apparatus 6 from contaminants and pathogens, while allowing sterilization of the support apparatus 6 using standard techniques. The support apparatus 6 may further include one or more fluid transfer conduits 60 (e.g., disposable tubing) that can supply separate isolated cooling, heating, and fluid/gas supply channels into and out of the support apparatus 6.

Containers are preferably designed to be rugged and to withstand shock resulting from falls etc. Containers may be made of any suitable material possessing requisite qualities, such as mechanical strength, bio-compatibility, heat tolerance, gas tolerance, and the ability to house both electronic componentry and biologic materials.

In some embodiments, radio frequency identification (RFID) technology can be used to keep track of the support apparatuses as well. The support apparatuses can be used as part of a network for transportation and delivery of the biological chip device to a hospital where the system can be tested to confirm cell viability. A device for testing may be portable (e.g., hand-held), and may interface with a support apparatus by available communication technology, such as blue tooth, or by directly plugging in to the support apparatus 6.

Figure 2:
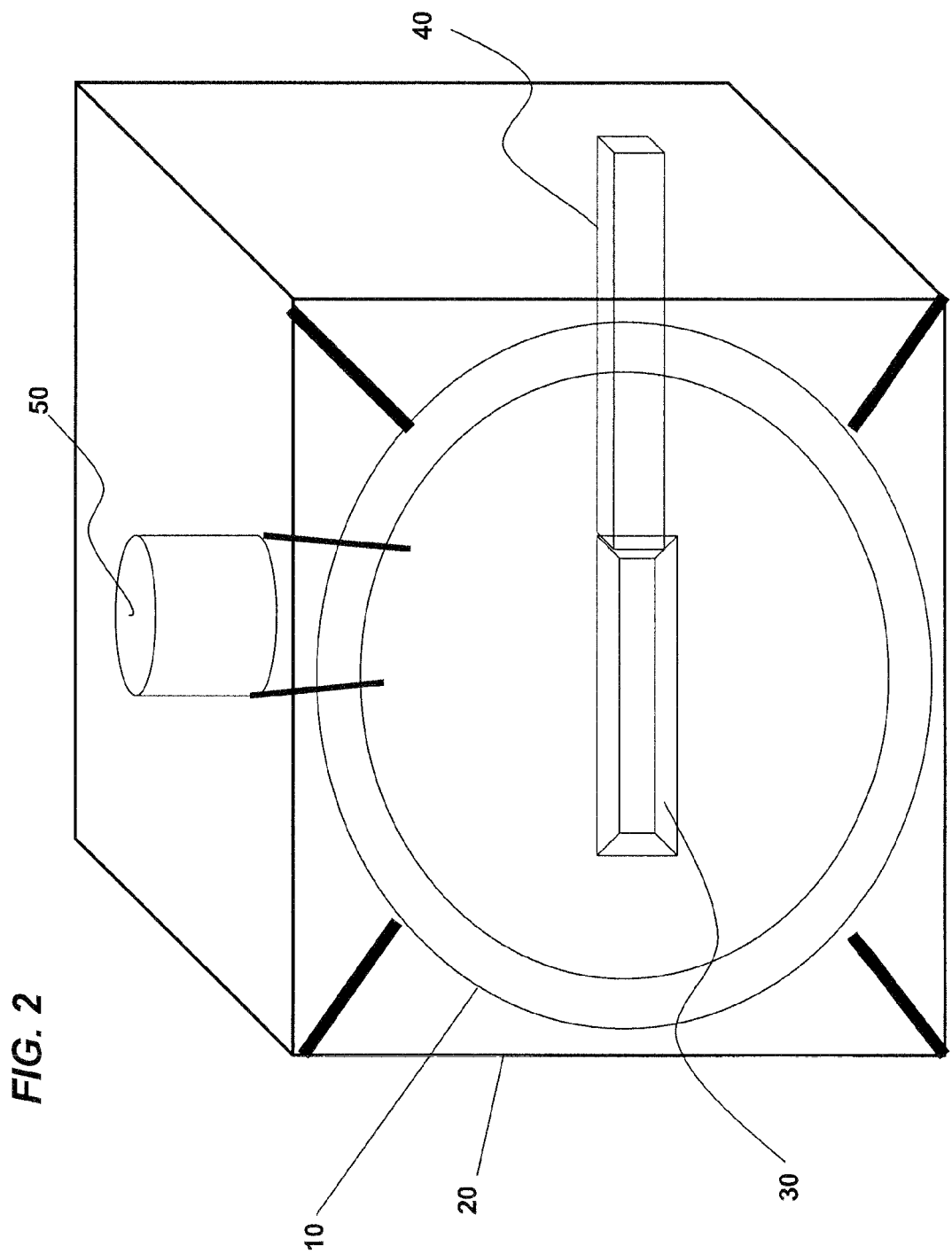
FIG. 2 is a schematic perspective view of a support apparatus for supporting, storing, and transporting biologic materials in accordance with embodiments of the invention.

FIG. 2 is a schematic perspective view of a biological materials support apparatus according to an embodiment of the invention. In the embodiment shown in FIG. 2, a generally spherical inner portion 10 is shown disposed within a generally rectangular (or cubed) outer portion 20. This may be useful, for example, in applications that require the biological chip device to be at least partially immersed in a fluid substance (e.g., to maintain at least partial fluid contact). This configuration may also be useful in applications where enhanced control of temperature at various sections of the spherical container is desired. A spherical inner portion 10 may provide for equidistant photonic or detection arrays surrounding the biological chip device 30, and may provide added security and/or stability by placing the device near the center of the spherical inner portion 10. The 3-dimensional rectangular/cubical outer portion 20 surrounding the inner portion 10 according to this embodiment of the invention may facilitate convenient storage and positioning of the support apparatus 6, and may be useful in embodiments of the invention where a plurality of support apparatuses 6 may be used (e.g., for stacking, interconnecting, storing, etc.).

With continued reference to FIG. 2, certain embodiments of the invention may include a housing having a generally spherical inner portion 10, which is adapted to maintain a particular orientation (e.g., vertical) regardless of the orientation of the support apparatus. For example, spherical inner portion 10 may be adapted to rotate freely relative to outer portion 20 (e.g., via a fluid support, bearings, and/or gimble arrangements and the like). Thus, inner portion 10 could be weighted, for example, near a bottom portion thereof to enable it to substantially maintain an orientation (e.g., to maintain an "upright" orientation due to gravitational effects). In embodiments of the invention where at least partial fluid contact is desired between biological materials and a fluid from a fluid source needed for providing a sustaining environment, the ability to maintain an "upright" orientation may facilitate such fluid contact by keeping the biological materials immersed in the fluid (provided sufficient fluid is present).

In some embodiments, the inner portion of the housing may be adapted to spin about a spin axis, or to spin about several axes. The spin axes may be adjustable, and may allow for the inner housing to rotate or spin in a continuous or intermittent manner, for example.

Figure 3A:
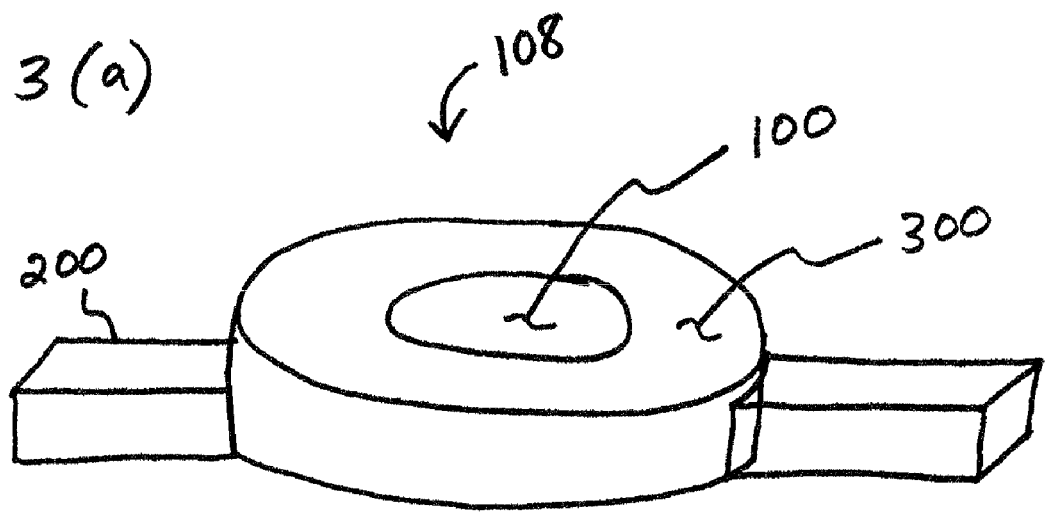
FIG. 3(a) is a schematic perspective view of an exemplary support apparatus having first and second chambers according to an embodiment of the invention.

FIG. 3(a) is a schematic perspective view of an embodiment of the invention having an exemplary support apparatus 108 comprising a first chamber (or housing) 100 and a second chamber 300. First chamber 100 is where a living matrix chip or biological chip device 30 may be physically secured and/or environmentally sustained. Second chamber 300 may provide the ability to control the environment (e.g., to provide a sustaining environment) within first chamber 100. This may be done with electrical coils (e.g., for heating) and/or a fluid controlled system (for heating and cooling) disposed within second chamber 300.

FIG. 3(a) also shows input/output path(s) 200, which provide flowpaths for the flow of various services to and from the first chamber 100 and/or second chamber 300. For example, an input/output path 200 may contain electrical components and wiring needed to supply electrical power from a source external to support apparatus 108 to a living matrix chip 30 disposed within first chamber 100. Input/output path 200 may also provide fluid flow to heating/cooling elements disposed within second chamber 300. For example, a "coolant" (e.g., chilled water, freon, liquid nitrogen, etc.) may flow via tubing, for example, through input/output path 200 into the second chamber 300, where it absorbs heat from the first chamber 100, then is returned via input/output path 200 to an external cooling source. In an embodiment with a single input/output path 200, for example, such coolant fluid flow may be routed to and from second chamber 300 via the single input/output path 200. Alternately, in embodiments, with two or more input/output paths 200, fluid flow may enter second chamber 300 at one point and may exit second chamber 300 at a different point, possibly allowing for better thermal characteristics (e.g., better heat transfer) according to some embodiments. Liquid nitrogen, for example, may be used as a "coolant" for controlled cooling of the first chamber 100. In an embodiment utilizing liquid nitrogen, one or more pressure release valves (not shown) may additionally be required to control evaporation and address other pressure-related issues. One embodiment for long-term cryogenic storage may include the ability to continuously cycle liquid nitrogen through several networked support apparatuses 108. The flow of nitrogen may be controlled by electronic valves adapted to supply the desired coolant flow to the desired support apparatuses 108 to achieve the desired temperature, for example.

Input/output path 200 may also be used to exchange fluid between the first chamber 100 and the environment external to the support apparatus 108. Such fluid exchange may be desirable in order to provide a sustaining environment to biological materials (e.g., living matrix chip 30) disposed within first chamber 100, and/or may provide the ability to communicate information to or from the living matrix chip 30.

Figure 3B:
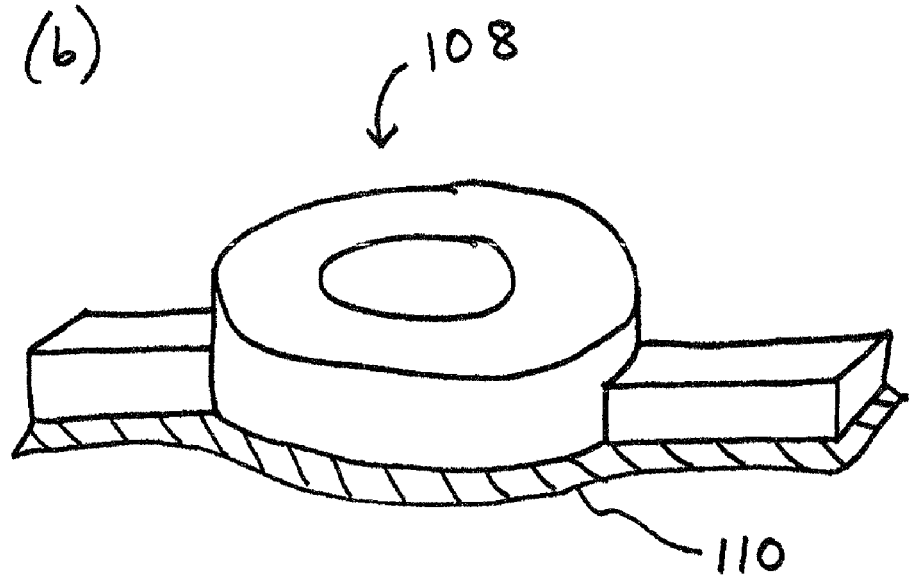
FIG. 3(b) includes an embodiment of the invention incorporating a vibration mount.

FIG. 3(b) shows a preferred embodiment of the invention having a vibration mount 110 coupled to the support apparatus 108 to absorb physical shock (i.e., acceleration-related forces) and vibrations, and to thereby protect the living matrix chip 30 from damage that may be caused by such motion.

Figure 4A:
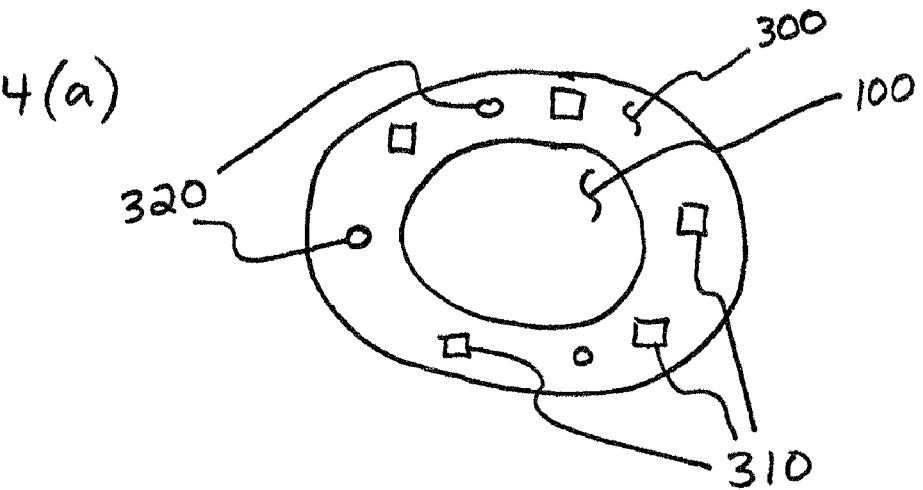
FIGS. 4(a), 4(b), and 4(c) are schematic views of an exemplary support apparatus according to embodiments of the invention.

FIG. 4(a) is a schematic top plan view showing a possible arrangement of components in second chamber 300. For example, bio-sensors 310 may be disposed within second chamber 300 to monitor a number of environmental parameters, such as temperature and pH, for example and without limitation. Bio-sensors 310 may also include photodetectors, for example, to monitor levels of radiated energy, such as visible light, ultraviolet and infrared energy, and other forms of radiated energy.

Photo-emitters 320 may also be disposed within second chamber 300 in certain preferred embodiments of the invention. In one embodiment, photo-emitters 320 may emit light at known or specified wavelengths. The response of cells in the living matrix chip 30 may then be monitored using bio-sensors 310. For example, infrared energy at specific wavelengths may be emitted by photo-emitters 320, and the response of cells may be monitored by a bio-sensor 310 (such as a photodetector) to determine or confirm the continued viability of the cells in a given living matrix chip 30. Bio-sensors 310 may further include enzymatic/chemical and/or photo-receptor/detectors, and/or temperature/pH sensors, and/or light/laser-based means for detecting changes in cell shape, density, or visible alterations in the fluid/gaseous environment. Electrical sensors may be employed to detect static electricity and/or electromagnetic interference (EMI) that may potentially damage the chip. Other cell sensing may occur at the chip level and may be relayed back to the container electronics, and possibly to a computer or processor connected thereto.

Cell activity, cell growth, and modulation of the release of chemical or biological signals by cells may be controlled using a supply of fluids (e.g., certain drugs) and/or emission of electromagnetic energy (typically light energy) at various selected frequencies (e.g., by photo-emitters 320). Since certain cells may be designed and/or selected to produce fluorescent proteins, for example, cells may be adapted to respond to the presence of those proteins. This interaction between cellular materials, in addition to stimuli from light energy and/or fluid supply (e.g., chemical or drug) may be employed to block an activity, trigger an activity, or amplify a response, among other possible examples. This interaction could be controlled, for example, using various wavelengths of light, as well as combining it with infusion of drugs or other substances that work alone or in conjunction with the light. A specific wavelength or intensity of electromagnetic energy (e.g., light) may cause release of biologic or chemical substances that are initially "caged" or bound, but may be released when exposed to specific energies and wavelengths. The same electromagnetic energy can also enhance binding of biologic or chemical substances together to, for example, inhibit their activity or enhance their function by creating a link between two substances. Cells may be selected to produce fluorescent proteins of various colors, for example, corresponding to certain wavelengths of light energy. Color-coding of cell responses may thereby be incorporated into the function of the support apparatuses. Green fluorescent protein (GFP) is one example of such a fluorescent protein, but many other colors are available.

Substances, such as drugs, chemicals, proteins, etc., can also be infused into first chamber 100 to exist in a dormant, inactive state, but may be "triggered" by a certain stimulus (or by certain combinations of stimuli). For example, exposure of the substance to light energy, ultrasound energy, or RF energy (among many possible examples), may cause biological materials and/or chemicals stored in such substances to be released from their bound configurations and become "bio-available" to the matrix cells for nutrition, activation, and for other purposes.

One example of an exemplary technology that may be employed to supply the above-mentioned types of substances to the cells of a biological chip device is nanotube technology. Carbon nanotubes, for example, may be used for the above-described chemical and drug-elution processes. Additionally, carbon nanotubes may serve to provide structural support for cells within support apparatus 8.

Nanotube technology can also be used in other portions of the support apparatus 6. For example, nanotubes can be used to form portions of fluid transfer conduit 60, such as the fluid pathways contained therein, or may form the conduit 60 itself. Nanotubes may be integrated into the wall of the piping or tubing between support apparatuses 6 to provide for controlled elution of drugs, chemicals, and/or other biochemical substances according to certain embodiments of the invention. Nanotube technology may thus facilitate flow-related release or delivery of chemical, drug, and biological substances, and may further facilitate the activated release of such substances using mechanisms (signals) such as heat, ultrasound, RF, magnetic field energy, and/or light energy stimulation. Alternatively, fluid flow from and to biological chip devices may be controlled (directed, shunted, bypassed, etc.) using valves, as well as circuitry that may be equipped with drug release mechanisms that may or may not use nanotube technology.

Figure 4B:
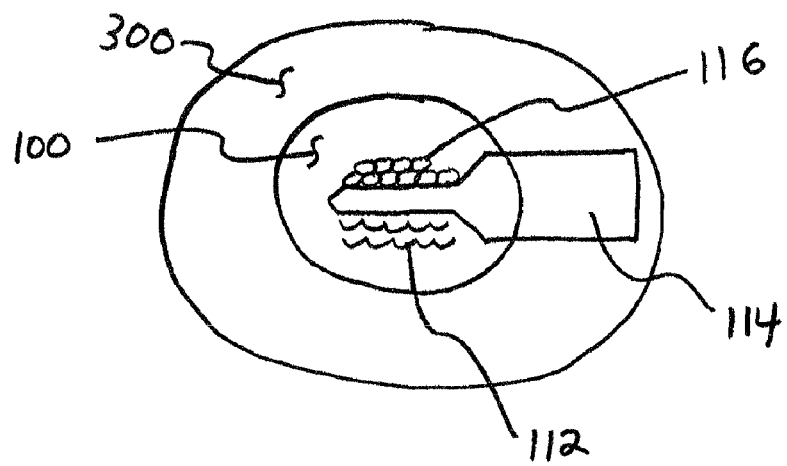
Figure 4C:
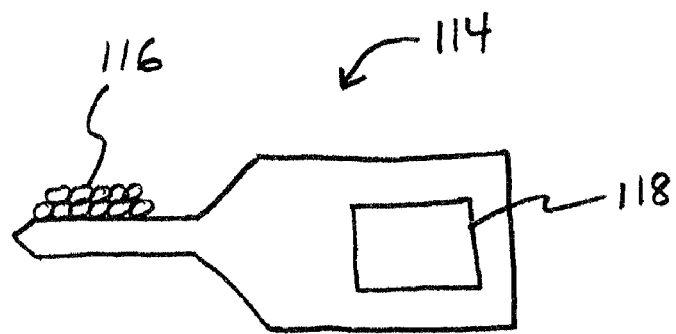

FIGS. 4(b) and 4(c) show on embodiment of the invention in which living cells 116 of a biological chip device are shown suspended and secured in first chamber 100 such that the living cells 116 are in contact with solution 112, which may be a saline, bio-supportive liquid, for example. As shown in FIG. 4(b), a support device 114 may physically support or suspend the living cells 116 in solution 112. The support device 114 may thereby provide protection to the living cells 116 from vibration, shock, or other forces. Further, support device 114 may provide the housing or support for electronics, electrical power, and communication signal pathways between the living cells and the external environment, as shown in the cross-sectional side view of FIG. 4(c).

Networked Devices

In certain embodiments of the invention, reusable containers can be networked to allow monitoring and control of hundreds or thousands of these chips by a processor or computer.

In addition, the ability to network individual chips that may have different types of biologic materials/cells integrated and thus detect and respond differently to various signals allows for the formation of an integrated live cell network. One can consider each matrix chip as a sensor or task specific processor and link them in such a way as to provide ability to route the information between various chips—to produce needed results or learning. The chips may communicate via RF, physical electrical connection, or photonic light communication. Sensing by the chip maybe electrical, mechanical or photonic.

In addition fluid channels may be constructed around each matrix chip's biological material to allow transfer of any solution including plasma, blood, and like substances to provide nutrients but also to provide the ability for cells to communicate between various matrices (each matrix within an isolated container or cluster of matrices within a container) by secreting chemical messengers in a dose and time dependent manner which is then detected as information and acted upon by other matrices within the system. This would provide the ability for cells to communicate with each other (i.e. networking) and can also communicate with external equipment outside using photonic, electrical, mechanical and chemical messages. The fluid system could form a network of "pipes," the flow of fluids through such pipes being controllable by small valves that shunt fluid which is the medium for carrying the chemical messengers. The shunting allows for the "signal" to be sent (or diverted) to wherever the operator wants or the software designates. These pipes can also be lined by photonic sensor and emitters that sample the fluid for concentrations of various substances and can also neutralize the signal if needed or inject additional substances for signal amplification, testing, control or calibration.

The above-described functionality may form the basis for a computer or processor to be built that is comprised, at least in part, of living cells in compartmentalized modules. It also provides the ability for mass storage of information and communication between matrix devices by providing various forms of communication. For example, cells may communicate with each other at a cellular level by carrying out a normal biological response to stimuli. A different form of communication, for example, may include fluorescence-based signaling, wherein a cell responds biologically to a stimulus by fluorescing, and the light emitted is then detected by photodetectors or other sensors as an electrical, logical, or information signal. This information may then be passed on to other components within a network of devices or modules. Yet another form of communication may be employed by actively delivering electrical stimulation, or light stimulation, or some other form of input stimulus to the biological material component of a biological chip device, and measuring or detecting the response. The various forms of communication possible may not be so easily distinguished as the systems become complex and the stimuli and response signals become mixtures of biological and electrical signals.

In certain embodiments of the invention, a support apparatus may include an energy transfer portion adapted to transfer electromagnetic energy (e.g., light energy or other optical signals) from the housing. As noted above, the electromagnetic energy being transferred from the housing can contain information about the cells, or information about changes in the cells, such as information about cell growth, cell shape, cell division, and cell function associated with the biological materials, and changes in these and similar cell parameters. The energy transfer portion of the support apparatus may transfer electromagnetic energy from the housing using photodetectors, for example, located in the space between inner and outer portions according to certain embodiments. Photodetectors may be selected according to their ability to sense and/or respond to light signals produced by the biological materials. For example, the energy transfer portion may include a photodetector adapted to sense light signals produced by one or more fluorescent proteins. Optionally, or additionally, the energy transfer portion may include a photodetector adapted to sense optical characteristics of light signals using such techniques as reflectometry, for example. Light signals may also be monitored and compared to reference or baseline signals, for example, to sense morphological changes in light signals, according to certain embodiments.

Various cell types, or cells with a range of different response characteristics, may be combined or mixed within a given module, or between interacting modules, to allow for the development of a broad array of sensing and stimulation capabilities. Genetic engineering of cells may make possible the ability to express specific cell receptor subtypes and/or cells having enhanced characteristics that may make them suitable for use in diagnostic applications (e.g., as part of a diagnostic tool), or as part of a computer network, for example and without limitation. The desired cell characteristics may also be obtained by techniques that include developing cells that are more biocompatible and that are well-suited for such an environment.

Figure 5A:
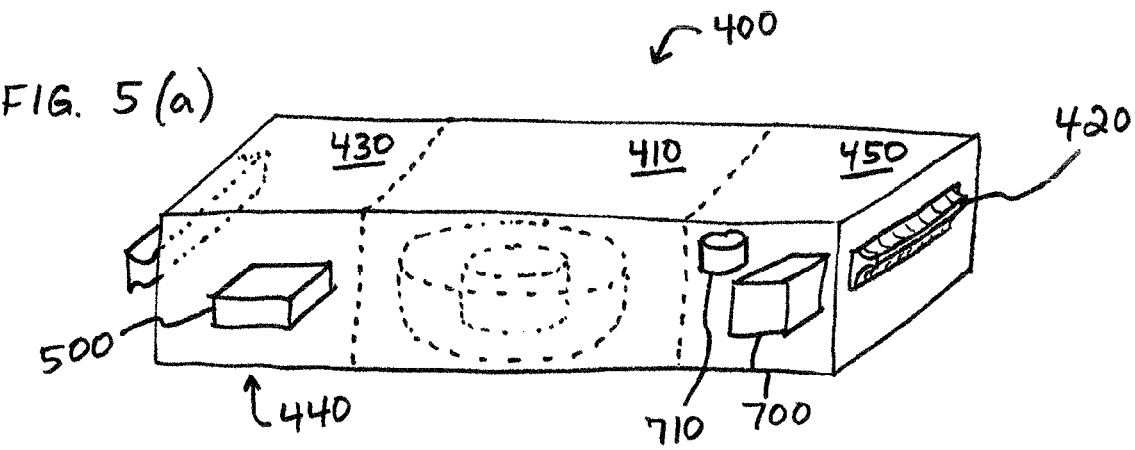
FIGS. 5(a), 5(b), and 5(c) include support apparatuses according to embodiments of the invention adapted to communicate with other devices.
Figure 5B:
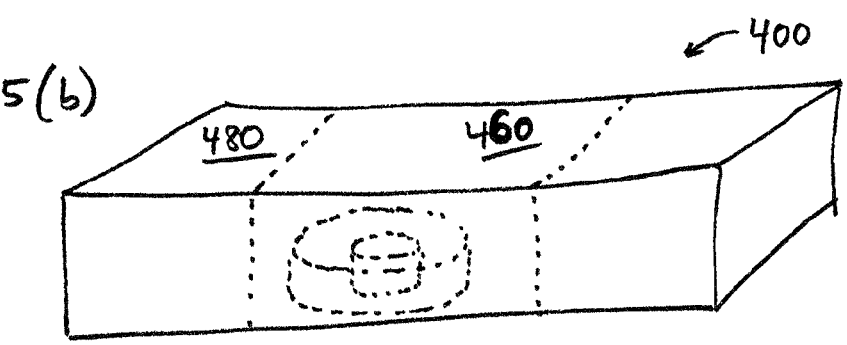
Figure 5C:
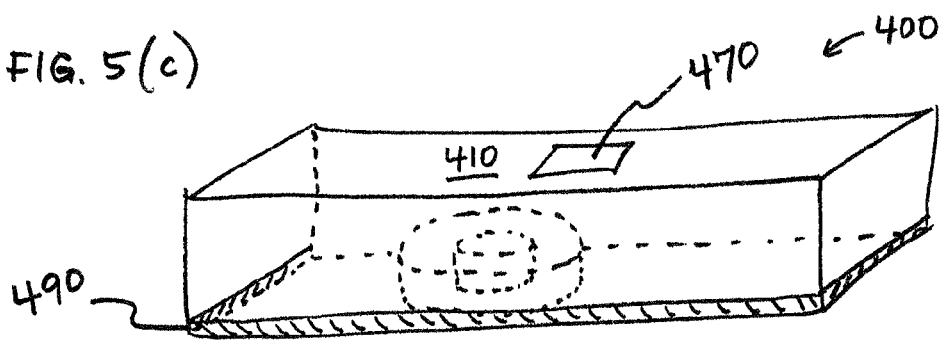

FIGS. 5(a)-(c) show several embodiments of the invention in which a support module 400 for supporting a living matrix chip 30 is designed to communicate with and/or interconnect with other devices or systems, including other support modules 400.

In the embodiment of FIG. 5(a), support module 400 comprises a first compartment 410, in which a biological chip device may be sustained. Support module 400 additionally includes an interconnector 420 to allow for physical interconnection of support module 400 with another device or system. Interconnector 420 may, for example, provide an interlocking fit with another device or system to secure support module 400 in place. Interconnector 420 may additionally have connections for providing electrical power to support module 400 (and the biological chip device supported thereby). A plurality of interconnectors 420 may be employed.

In certain embodiments, interconnector 420 may also possess wiring or circuitry to allow for the transfer of information (i.e., communication of signals: electrical, electronic, optical, RF, etc.) to and from the biological chip device within support module 400. In still further embodiments, interconnector 420 may provide pathways or conduits that enable fluid transfer between support module 400 and the external environment, for example, to supply nutrients, remove waste products (e.g., carbon dioxide), or provide flow of heating or cooling fluids to control temperature within support module 400. In some embodiments, a plurality of interconnectors 420 may be disposed about the support module to accomplish the above-described functions.

The embodiment of FIG. 5(a) further shows the addition of an optional second compartment 430, which is a "dry" compartment in one preferred embodiment. Second compartment 430 may, according to other preferred embodiments, further include power supply 500, which supplies electrical energy to first compartment 410. Electrical energy from power supply 500 may be a DC voltage, perhaps on the order of 12 volts DC. Certain embodiments may require higher outputs voltages, or a plurality of voltage levels supplied in order to meet the system requirements. A transformer may be employed to supply power from AC sources, delivering an appropriate level of DC voltage to supply power or to re-charge power supply 500. Power supply 500 may be rechargeable; access to the power supply 500 may be enabled by the inclusion of access door 440 formed in a surface of second compartment 430, for example.

In one embodiment, a nutrient supply 700 and fluid gas containers 710 may be housed in second compartment 430 (not shown). FIG. 5(a) shows a third compartment 450, which may be present in certain alternate embodiments. In the embodiment of FIG. 5(a), third compartment 450 may be a dry compartment with a supply of nutrients 700 and containers 710 for fluid/gas storage and exchange with the first compartment 410.

FIG. 5(b) shows an embodiment including a "wet" compartment. This embodiment provides several compartments within a single container. For example, a "wet" compartment 460 may be one in which the biological chip device 30 is stored and in which living cells are sustained. The one or more compartments surrounding it may be "dry" compartments 480, for example, which may provide for the electrical connections between the biological chip device 30 and the support apparatus 8. There may typically be less heating and less risk of electrical noise interference with electrical components (such as MEMS components) in such a dry compartment 480. A "dry" compartment may also house electrically noisy, heat-generating components, such as a battery, transformer, etc. In a preferred embodiment of the invention, a separate dry compartment 480 (located further away from living cells, for example) may be used to house such electrically noisy, warm components.

FIG. 5(c) is a perspective view of a support apparatus or support module 400 according to an embodiment of the invention in which a biological chip device is mounted within support module 400 using a vibration absorbing mount 490. The vibration absorbing mount 490 may comprise a resilient structure that couples the biological chip device to the support module 400 in a manner that isolates or reduces mechanical forces, such as vibration, from being directly transmitted to the biological chip device. In one embodiment, a resilient lining placed in the first compartment 410 (e.g., a wet compartment) may form vibration absorbing mount 490, with the biological chip device 30 mounted thereto. In certain embodiments a vibration absorbing mount 490 may also serve as a thermal insulation layer. Also shown in FIG. 5(c) is a window 470 that allows for visual inspection of the interior of the first compartment 410. In certain preferred embodiments, window 470 may include a wavelength-specific or wavelength-limited filter to prevent light (or other electromagnetic energy) that may be harmful to the living cells inside first compartment 410, from reaching those cells. Further, the filter may prevent the entry of energy into the first compartment 410 that may interfere with the aforementioned diagnostic capabilities of the device.

Figure 6A:
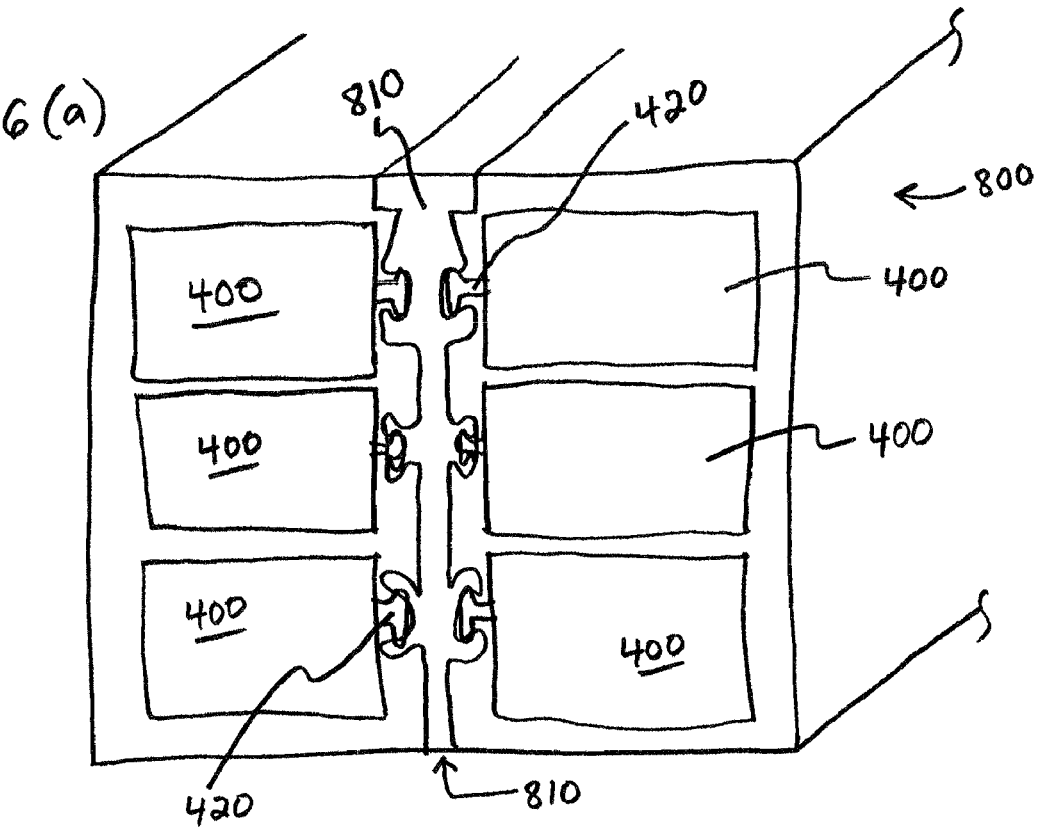
FIGS. 6(a) and 6(b) include support apparatuses adapted to function as part of a network of such devices according to various embodiments of the invention.

FIG. 6(a) is a schematic representation of a system 800 of "networked" support modules 400. The interconnectors 420 of each support module 400 is "plugged" into a backbone 810 of system 800. System 800 may provide a structure that facilitates the formation of networks of support modules 400 that may be designed to perform functions ordinarily performed by electronic circuitry. Examples of such function may include, but are not limited to: communications, binary representation of information, logical operations, etc. Different cells may thereby provide different responses to approximate values in a circuit, for example.

System 800 may provide for the sharing of services by the support modules 400. System 800 may provide for the physical connection of multiple modules or containers. The connection may include not only physical connection, but may also include shared electronic communication and fluid exchange between containers. Fluid exchange may further include the exchange of biochemical information between containers. System 800 may provide power for a group of connected modules, centralized control of environmental parameters, and diagnostics for individual modules. Additionally, heating and/or coolant materials, nutrient supply, and waste removal may be controlled centrally by system 800.

Figure 6B:
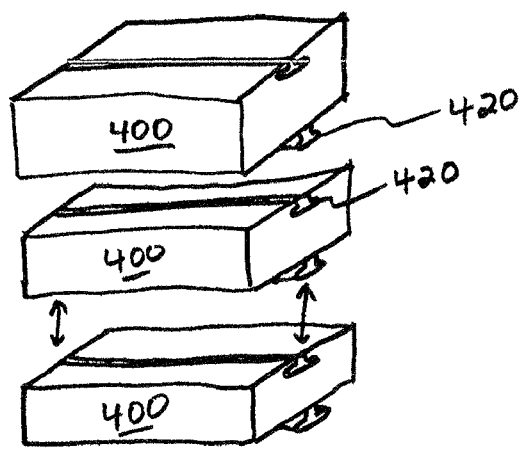

FIG. 6(*b*) illustrates a vertical stacking arrangement of support modules 400 according to an embodiment of the invention. The linking of modules can take several forms, including local stacking and/or topographical (horizontal) linking. Further, a certain number or configuration of modules may be linked together to form "clusters," and such clusters may be networked to other clusters in a variety of ways, including via an internetwork (similar to, or as part of the Internet). Clusters may also communicate via standard electronic communication protocols (analog and digital), including both wired and wireless (e.g., radio frequency, "RF") communications.

The system 800 and its backbone 810 allow for the simultaneous monitoring, storage, and control of the environmental parameters that affect the living matrix chips 30 (i.e., living cell devices in the support modules 400. The system 800 may also allow for communication between modules. In a further embodiment, system 800 may be further adapted to interconnect with an external computer 900 (for example, a personal computer). Communication between support modules 400 may be alternately or additionally provided in the form of fluid channels that provide flow between support modules 400; backbone 810 of system 800 may also provide fluid flow paths (conduits) to supply this functionality.

The system can open/close fluid valves to shunt chemicals from cells or injected into system from outside to specific modules to run specific algorithms. The opening and closing of fluid valves may itself be a function of cellular responses to signals. For example, certain embodiments of the invention may include support apparatuses which can function as flow control valves, opening or closing (e.g., restricting fluid flow) by activation of certain biological materials (e.g., muscular cells) with appropriate stimuli. In a particular embodiment, cells may be formed around a flexible fluid flow path, and activation of such cells (e.g., by electromagnetic stimulus) may cause a restriction in the fluid flow path due to a coordinated contraction of the muscular cells in response to the stimulus, for example. In certain other embodiments, a fluid pump may be formed in an analogous manner.

Many combinations of signals may exist, because information (such as a fluorescent response at a specific wavelength) does not exist in isolation, but is often part of an overall larger informational picture that includes complex interactions with other data related to the cell response. Specifically, since cells are able to detect and process many signals concurrently, and since different types of cells may be used to obtain different responses, the number of permutations and combinations of responses and functions made possible thereby is very large. Examples of different signals and responses possible may include combining chemical signals with other cell responses, such as electrical and/or photonic responses, or cell movement information, such as that related to contractility.

The support modules (support apparatuses) may have the capability to be physically linked for storage (similar to the way in which multiple computer servers may be mounted in a rack system). The modules may further have the ability to communicate wirelessly with RF, optical communications, or using the chemical signaling that is possible when the modules are linked via a tubing system allowing biochemical substances to move between various modules. Control of communications flow may be performed at a local level (i.e., within system 800), or at an external location (i.e., an external computer) for further data processing, if desired.

The chamber in which the biological materials live (e.g., first compartment 410) may require fluid/solution to be pumped in and out (for exchange of nutrients, oxygen, other gases, etc., and removal of waste).

This fluidic system can be connected between support modules to allow control of fluid flow in a sequence and time-dependent manner between modules as well as allow the solution to be tested externally for chemicals, substances, etc.

The ability to network a plurality of modules may allow cell signals that are in chemical form such as hormones, peptides and other blood-based substances to be available to other members (modules/cells) within the network. This would allow for physiologic communication between modules/cells and allow for cells to respond (e.g., cell-based computing diagnostics). A cell-based processor or computer can thus be made from an interconnection of support modules and selection of cell types, and/or "wiring" them to provide the desired communication of information.

In certain embodiments, an implantable medical device (IMD) may be formed from a network of support apparatuses, using one or more apparatuses to perform sensing and/or testing functions (e.g., to sense a physiological parameter such as blood-sugar level in a patient), for example, and using one or more apparatuses to form a cell-based processor and/or therapy delivery subsystem, which may determine an appropriate response to a sensed input and provide the desired response (e.g., delivery of insulin to the patient via a cell-based infusion pump). In certain embodiments, a wearable device may be similarly formed from one or more support apparatuses (or from a network of support apparatuses), to perform sensing and/or testing functions, for example, manual (patient-activated) testing of blood parameters such as blood sugar level. Some embodiments may combine the use of both an IMD and a wearable (or portable) device to allow manually initiated functions to be performed. In one possible embodiment, a patient may place a portable device near an implanted IMD, and communications between the two may be established (e.g., wireless, magnetic, RF, etc.), allowing a patient to "trigger" a particular testing or sensing function. In some embodiments, the test result may be communicated to the portable device for visual display, and may be further communicated to other devices for recording and/or performing actions in response to the measured test result.

Figure 7:
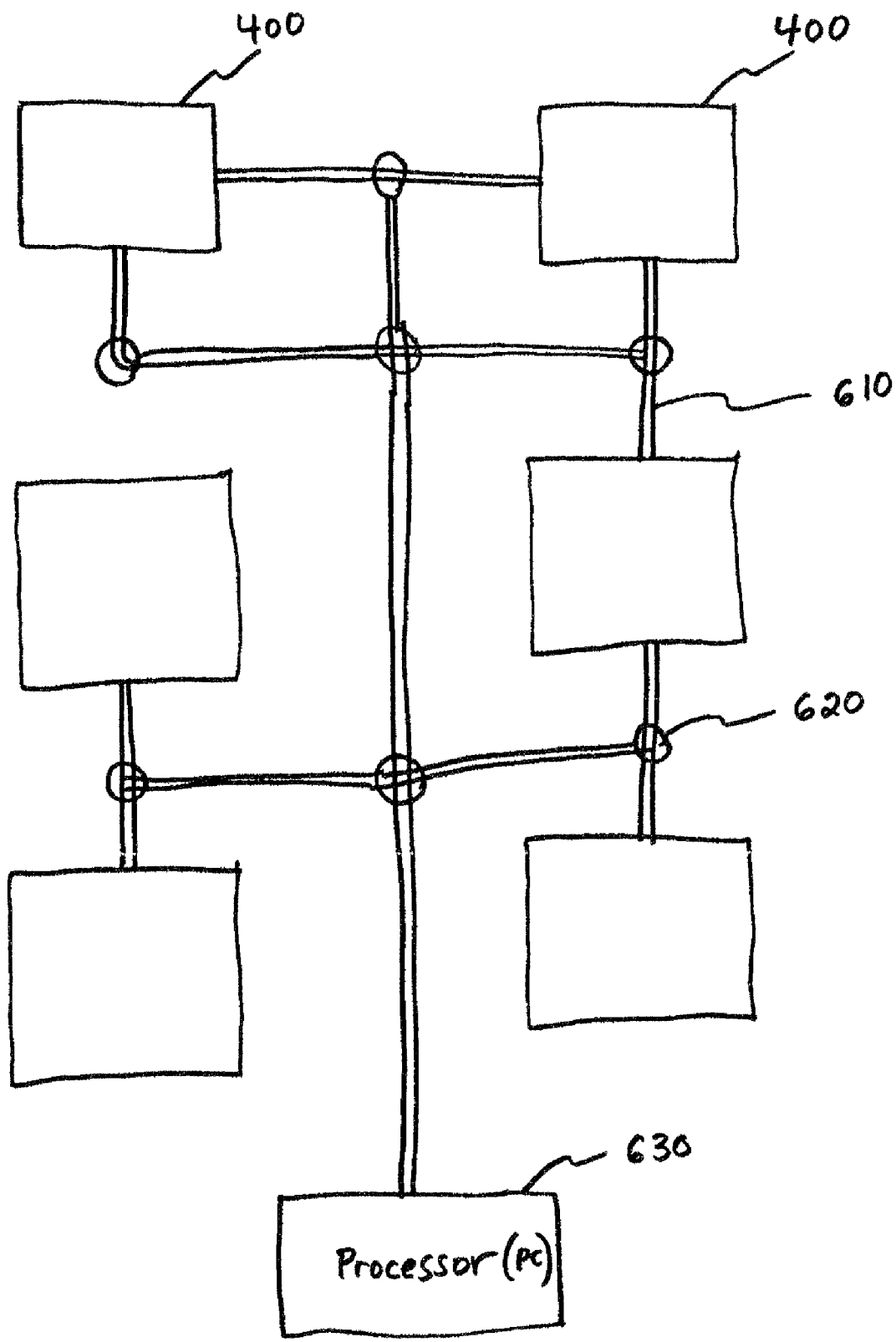
FIG. 7 is a block diagram of an exemplary network of support apparatuses showing possible exemplary fluid interconnections between support apparatuses according to certain embodiments of the invention.

FIG. 7 illustrates the formation of a circuit or network comprising a plurality of support modules 400 connected via tubing 610 and valves 620 to allow fluid communication therebetween. Additionally, signals to control the opening and closing of valves 620 may be sent from support modules 400, or from a processor 630 (e.g., a computer or microprocessor-based system), for example, according to a software instruction or process step.

Thus, embodiments of a system, method, and apparatus for supporting, storing, and transporting biological materials are disclosed. One skilled in the art will appreciate that the present invention can be practiced with embodiments other than those disclosed. The disclosed embodiments are presented for purposes of illustration and not limitation.

What is claimed is:

1. An apparatus for supporting biological materials, the apparatus comprising: a housing for providing a sustaining environment to biological materials which may be placed therein, wherein the housing comprises an inner portion and an outer portion, the inner portion being disposed within the outer portion to form a space therebetween, wherein the inner portion of the housing is adapted to provide the sustaining environment to a three-dimensional arrangement of living cells, and wherein the space between the inner and outer portions of the housing includes a gel having desired thermal characteristics; a fluid source for supplying a fluid to the sustaining environment in the housing; a nutrient source for supplying nutrients to the sustaining environment in the housing; an excitation emitter for transferring energy to the housing; and an energy transfer portion for transferring energy from the housing.

2. The apparatus of claim 1 wherein the space between the inner and outer portions of the housing includes a thermal control element.

3. The apparatus of claim 1 wherein the space between the inner and outer portions of the housing includes an environmental sensor.

4. The apparatus of claim 1 wherein the housing is adapted to maintain the fluid in the sustaining environment in at least partial fluid contact with biological materials being supported within the housing.

5. The apparatus of claim 1 wherein the fluid is in a phase selected from the group consisting of liquid, gas, and plasma.

6. The apparatus of claim 4 wherein the fluid is at least partially a liquid, the liquid adapted to be in contact with biological materials being supported within the housing by occupying more than a specified volume of the inner portion of the housing.

7. The apparatus of claim 4 further comprising a holding portion for holding the biological materials, the holding portion located within the inner portion to facilitate fluid contact with biological materials being supported within the housing.

8. The apparatus of claim 7 wherein fluid contact with biological materials is maintained regardless of orientation of the apparatus.

9. The apparatus of claim 8 wherein the inner portion of the housing is generally spherical.

10. The apparatus of claim 1 wherein the inner portion is adapted to substantially maintain an orientation within the apparatus due to gravitational effects.

11. The apparatus of claim 1 wherein the housing comprises a biocompatible enclosure.

12. The apparatus of claim 11 wherein the enclosure is adapted to form a watertight seal.

13. The apparatus of claim 1 wherein the biological materials to be supported include a biological materials component of a biological chip device.

14. The apparatus of claim 4 wherein the sustaining environment provides a liquid and gas interface for the biological materials to be supported.

15. The apparatus of claim 1 wherein the inner portion of the housing is adapted to spin about a spin axis.

16. The apparatus of claim 15 wherein the spin axis is adjustable.

17. The apparatus of claim 15 wherein the inner portion is adapted to spin continuously.

18. The apparatus of claim 15 wherein the inner portion is adapted to spin intermittently.

19. The apparatus of claim 1 further comprising a fluid transfer conduit for providing the fluid supplied by the fluid source to a fluid exchange.

20. The apparatus of claim 19 wherein the fluid exchange is located within the inner portion.

21. The apparatus of claim 1 wherein at least one of the nutrient source and fluid source is a fluid pump.

22. The apparatus of claim 21 wherein the fluid pump is a hydrostatic pump.

23. The apparatus of claim 21 wherein the fluid pump is an osmotic pump.

24. The apparatus of claim 21 wherein the fluid pump is powered by gravity.

25. The apparatus of claim 21 wherein the fluid pump provides a pulsatile flow.

26. The apparatus of claim 1 further comprising a connection strut for coupling a biological chip device disposed within the inner portion to external services.

27. The apparatus of claim 1 wherein the excitation emitter is an electromagnetic energy source.

28. The apparatus of claim 27 wherein the electromagnetic energy source is selected from the group consisting of light, electrical, and radiation sources.

29. The apparatus of claim 1 wherein the excitation emitter is a mechanical energy source.

30. The apparatus of claim 1 wherein the excitation emitter is a thermal energy source.

31. The apparatus of claim 1 wherein the energy transferred to the housing by the excitation emitter is used to trigger an event.

32. The apparatus of claim 1 wherein the energy transfer portion is adapted to transfer electromagnetic energy from the housing.

33. The apparatus of claim 32 wherein the electromagnetic energy being transferred from the housing contains information about any of cell growth, cell shape, cell division, and cell function associated with the biological materials.

34. The apparatus of claim 32 wherein the electromagnetic energy is transferred from the housing photodetectors.

35. The apparatus of claim 34 wherein the photodetectors are adapted to sense light signals provided by the biological materials.

36. The apparatus of claim 35 wherein the photodetectors are adapted to sense light signals provided by one or more fluorescent proteins.

37. The apparatus of claim 36 wherein the photodetectors are adapted to sense light signals provided by green fluorescent protein.

38. The apparatus of claim 35 wherein the photodetectors are adapted to sense optical characteristics of light signals from the biological materials.

39. The apparatus of claim 38 wherein optical characteristics of light signals are sensed using reflectometry.

40. The apparatus of claim 38 wherein light signals are compared to a baseline signal.

41. The apparatus of claim 35 wherein the photodetectors are adapted to sense morphological changes in light signals from the baseline signal.

42. The apparatus of claim 1 wherein the energy transfer portion is adapted to transfer mechanical energy from the housing.

43. The apparatus of claim 42 wherein the mechanical energy is sensed using one or more stress/strain gages.

44. The apparatus of claim 1 wherein the energy transfer portion is adapted to transfer thermal energy from the housing.

45. The apparatus of claim 44 wherein thermal energy from the housing is sensed using thermocouples.

* * * * *